(12) United States Patent
Wilson, Jr.

(10) Patent No.: US 6,863,675 B2
(45) Date of Patent: Mar. 8, 2005

(54) LIGATING CLIP WITH INTEGRAL PENETRATING HOOK

(75) Inventor: Donald F. Wilson, Jr., Raleigh, NC (US)

(73) Assignee: Pilling Weck Incorporated, Limerick, PA (US)

( * ) Notice: Subject to any disclaimer, the term of this patent is extended or adjusted under 35 U.S.C. 154(b) by 215 days.

(21) Appl. No.: 10/251,182

(22) Filed: Sep. 20, 2002

(65) Prior Publication Data

US 2004/0059359 A1 Mar. 25, 2004

(51) Int. Cl.⁷ .............................................. A61B 17/04
(52) U.S. Cl. ...................................... 606/157; 606/158
(58) Field of Search .................................. 606/157, 158

(56) References Cited

U.S. PATENT DOCUMENTS

| | | | |
|---|---|---|---|
| 3,270,745 A | 9/1966 | Wood | 128/325 |
| 3,326,216 A | 6/1967 | Wood | 128/325 |
| 3,363,628 A | 1/1968 | Wood | 128/325 |
| 3,439,522 A | 4/1969 | Wood | 72/410 |
| 3,439,523 A | 4/1969 | Wood | 72/410 |
| 4,294,355 A | 10/1981 | Jewusiak et al. | 206/339 |
| 4,509,518 A | 4/1985 | McGarry et al. | 128/325 |
| 4,579,118 A | 4/1986 | Failla | |
| 4,834,096 A | 5/1989 | Oh et al. | 128/325 |
| 5,062,846 A | 11/1991 | Oh et al. | 606/158 |
| 5,100,416 A | 3/1992 | Oh et al. | 606/139 |
| 5,509,920 A | 4/1996 | Phillips et al. | 606/157 |
| 6,391,035 B1 | 5/2002 | Appleby et al. | 606/142 |

Primary Examiner—Gary Jackson
(74) Attorney, Agent, or Firm—Jenkins, Wilson & Taylor, P.A.

(57) ABSTRACT

A polymeric, surgical clip having first and second curved leg members joined at their proximal end by a hinge portion and movable from an open position to a closed position for clamping a vessel between curved deposing inner surfaces which are substantially parallel when the clip is closed. The first leg terminates at its distal end in a deflectable hook member defining a crest or cutting edge along at least a portion of the outer surface thereof, and the second leg member terminates in a locking portion complimentary to the hook member such that when the first and second leg members are moved from an open position to a closed position about the hinge means the hook member will deflect about the distal end of the second leg member to lock the clip in a closed position. The deflection of the hook member will serve to cut connective tissue adjacent a vessel or the like to be clamped when the leg members are closed to aid in locking the clip in the closed position about the vessel or the like to which the surgical clip is applied.

6 Claims, 6 Drawing Sheets

LIGATING CLIP WITH INTEGRAL PENETRATING HOOK

TECHNICAL FIELD

The present invention relates to surgical clips, and more particularly to ligating clips with integral penetrating hooks to facilitate cutting connective tissue adjacent a vessel or the like to be clamped by the surgical clip to aid in locking the surgical clip in a closed position. Yet more particularly, the present invention relates to an improved surgical ligating clip which is provided with a cutting edge on the outer surface of the hook member which serves to slice through connective tissue adjacent a vessel or the like to be clamped as the leg members of the surgical ligating clip are closed to bring the clip into a closed and locked position.

BACKGROUND ART

Many surgical procedures require vessels or other tissues of the human body to be ligated during the surgical process. For example, many surgical procedures require cutting blood vessels (e.g., veins or arteries), and these blood vessels may require ligation to reduce bleeding. In some instances, a surgeon may wish to ligate the vessel temporarily to reduce blood flow to the surgical site during the surgical procedure. In other instances a surgeon may wish to permanently ligate a vessel. Ligation of vessels or other tissues can be performed by closing the vessel with a ligating clip, or by suturing the vessel with surgical thread. The use of surgical thread for ligation requires complex manipulations of the needle and suture material to form the knots required to secure the vessel. Such complex manipulations are time-consuming and difficult to perform, particularly in endoscopic surgical procedures, which are characterized by limited space and visibility. By contrast, ligating clips are relatively easy and quick to apply. Accordingly, the use of ligating clips in endoscopic as well as open surgical procedures has grown dramatically.

Various types of hemostatic and aneurysm clips are used in surgery for ligating blood vessels or other tissues to stop the flow of blood. Such clips have also been used for interrupting or occluding ducts and vessels in particular surgeries such as sterilization procedures. Typically, a clip is applied to the vessel or other tissue by using a dedicated mechanical instrument commonly referred to as a surgical clip applier, ligating clip applier, or hemostatic clip applier. Generally, the clip is left in place after application to the tissue until hemostasis or occlusion occurs. At some point thereafter, the clip is removed by using a separate instrument dedicated for that purpose, i.e., a clip removal instrument.

Ligating clips can be classified according to their geometric configuration (e.g., symmetric clips or asymmetric clips), and according to the material from which they are manufactured (e.g., metal clips or polymeric clips). Symmetric clips are generally "U" or "V" shaped and thus are substantially symmetrical about a central, longitudinal axis extending between the legs of the clip. Symmetric clips are usually constructed from metals such as stainless steel, titanium, tantalum, or alloys thereof. By means of a dedicated clip applier, the metal clip is permanently deformed over the vessel. An example of one such clip is disclosed in U.S. Pat. No. 5,509,920 to Phillips et al. An example of a metallic clip applier is disclosed in U.S. Pat. No. 3,326,216 to Wood in which a forceps-type applier having conformal jaws is used to grip and maintain alignment of the clip during deformation. Such appliers may additionally dispense a plurality of clips for sequential application, as disclosed in U.S. Pat. No. 4,509,518 to McGarry et al.

With the advent of high technology diagnostic techniques using computer tomography (CATSCAN) and magnetic resonance imaging (MRI), metallic clips have been found to interfere with the imaging techniques. To overcome such interference limitations, biocompatible polymers have been increasingly used for surgical clips. Unlike metallic clips, which are usually symmetric, polymeric clips are usually asymmetric in design and hence lack an axis of symmetry. Inasmuch as the plastic clip cannot be permanently deformed for secure closure around a vessel or other tissue, latching mechanisms have been incorporated into the clip design to establish closure conditions and to secure against re-opening of the vessel. For example, well known polymeric clips are disclosed in U.S. Pat. No. 4,834,096 to Oh et al. and U.S. Pat. No. 5,062,846 to Oh et al., both of which are assigned to the assignee of the present invention. These plastic clips generally comprise a pair of curved legs joined at their proximal ends with an integral hinge or heel. The distal ends of the curved legs include interlocking latching members. For example, the distal end of one leg terminates in a lip or hook structure into which the distal end of the other leg securely fits to lock the clip in place.

The distal ends of the clips taught by Oh et al. also include lateral bosses that are engaged by the jaws of the clip applier. A clip applier specifically designed for asymmetric plastic clips is used to close the clip around the tissue to be ligated, and to latch or lock the clip in the closed condition. In operation, the jaws of this clip applier are actuated into compressing contact with the legs of the clip. This causes the legs to pivot inwardly about the hinge, thereby deflecting the hook of the one leg to allow reception therein of the distal end of the other leg. A clip applier designed for use with asymmetric plastic clips in an open (i.e., non-endoscopic) surgical procedure is disclosed in U.S. Pat. No. 5,100,416 to Oh et al., also assigned to the assignee of the present invention.

In addition to compatibility with sophisticated diagnostic techniques, asymmetric clips have other advantages over symmetric clips. For example, because asymmetric clips are formed from polymeric materials, the mouths of asymmetric clips can be opened wider than the mouths of symmetric clips. This allows a surgeon to position the clip about the desired vessel with greater accuracy. In addition, a clip of the type described in U.S. Pat. Nos. 4,834,096 and 5,062,846 can be repositioned before locking the clip on the vessel or before removing the clip from the vessel, in a process referred to as "approximating" the clip.

Although plastic ligating clips are well known in the surgical area and improvements have been made to the ligating clips including providing a sharp protruding distal tip to the hook end in an effort to provide a penetrating plastic ligating clip (see, for example, the aforementioned U.S. Pat. Nos. 4,834,096 and 5,062,846). It would be desirable, however, to produce an improved polymeric surgical ligating clip with an integral penetrating hook which is particularly well suited for use to close vessels connected to surrounding tissue. The present invention is believed to provide such an improved surgical clip.

DISCLOSURE OF THE INVENTION

In accordance with the present invention, a polymeric surgical clip is provided of the type comprising first and second leg members joined at their proximal ends by a resilient hinge means. Each leg member has a vessel clamping inner surface and an opposite outer surface, and the vessel clamping inner surface is in opposition to the vessel clamping inner surface of the other leg member. The first leg member terminates at its distal end in a deflectable hook member curved toward the second leg member, and the second leg member terminates at its distal end in a locking portion complimentary to the hook member such that when the first and second leg members are moved from an open position to a closed position about the hinge means, the hook member deflects about the distal end of the second leg member to lock the clip in a closed position. The hook member has a continuously curved outer surface extending distally from the outer surface of the first leg member, side surfaces and an inner surface. The improvement to the polymeric surgical clip comprises providing the continuously curved outer surface of the hook member with two convex surfaces extending distally from the inner surface and inwardly from each side surface of the hook member so that the two convex surfaces define a crest or cutting edge therebetween that extends along the length of at least a portion of the outer surface of the hook member. In this fashion, connective tissue adjacent a vessel or the like to be clamped by the surgical clip is cut by the crest or cutting edge of the hook member when the leg members are closed to aid in locking the surgical clip into the closed position around the vessel or the like.

The surgical clip of the present invention is preferably made of polymeric material and accordingly minimizes interference with high technology diagnostic modalities such as CAT SCAN, MRI and MRS. At the same time, the clip is nearly as small as comparable metal clips while maintaining sufficient strength and possessing high security in the clip's latching mechanism in the closed position clamping the vessel. The surgical clip is configured to provide a secure means of handling an application to avoid premature release from the applier of the clip, and includes a hook member with an integral cutting edge for penetrating through surrounding tissue connected to the vessel or the like to be clamped by the surgical clip.

It is therefore an object of the present invention to provide a polymeric surgical clip capable of occluding a vessel adjacent or attached to connective tissue.

It is another object of the present invention to provide a surgical clip with an improved hook member having an integral cutting surface which serves to cut connective tissue adjacent a vessel or the like to be clamped when the leg members of the surgical clip are closed and locked together.

It is still an object of the present invention to provide a polymeric surgical ligating clip which is provided with an integral cutting edge on the hook member thereof to penetrate through connective tissues as the hook member deflects during closure of the surgical clip and to thereby facilitate closure of the surgical ligating clip around a vessel or the like.

It is still a further object of the present invention to provide a polymeric surgical ligating clip wherein the leading edge of the protruding hook member comprises a cutting edge defined by two intersecting convex surfaces such that as the surgical clip is closed the leading edge of the hook member contacts connected tissue and slices therethrough as the clip leg connected to the hook member deforms during latching of the two legs of the surgical clip into a closed and locked position.

Some of the objects of the invention having been stated hereinabove, other objects will become evident as the description proceeds when taken in connection with the accompanying drawings as best described hereinbelow.

DETAILED DESCRIPTION OF THE INVENTION

Referring now to FIGS. 1–6, one example is illustrated of an asymmetric surgical clip, generally designated 12, that is suitable for use in conjunction with the present invention. Clip 12 and others of similar design are particularly useful as hemostatic clips that can be latched around a vessel or other type of tissue to ligate the vessel and thereby stop or reduce the flow of fluid through the vessel. Clip 12 can be constructed from any suitable biocompatible material, such as certain metals and polymers. However, the present invention is particularly suitable for practice with polymeric clips. Thus, clip 12 preferably comprises a one-piece integral polymeric body formed from a suitable strong biocompatible engineering plastic such as the type commonly used for surgical implants. Examples include polyethylene terephthalate (PET), polybutylene terephthalate (PBT), polyoxymethylene, or other thermoplastic materials having similar properties that can be injection-molded, extruded or otherwise processed into like articles.

The body of clip 12 comprises a first or outer leg, generally designated 22, and a second or inner leg, generally designated 24. First and second legs 22 and 24 are joined at their proximal ends by an integral hinge section, generally designated 26. First and second legs 22 and 24 have complementary arcuate profiles. Thus, first leg 22 has a concave inner surface 28 and a convex outer surface 30, and second leg 24 has a convex inner surface 32 and a concave outer surface 34. Convex inner surface 32 of second leg 24 and concave inner surface 28 of first leg 22 have substantially matching radii of curvature. Hinge section 26 has a continuous concave inner surface 36 and a continuous convex outer surface 38. Concave inner surface 36 of hinge section 26 joins concave inner surface 28 of first leg 22 and convex inner surface 32 of second leg 24. Convex outer surface 38 of hinge section 26 joins convex outer surface 30 of first leg 22 and concave outer surface 34 of second leg 24. First leg 22 transitions to a curved, C-shaped hook section 40 at its distal end. Second leg 24 transitions to a pointed tip section 42 at its distal end. Hook section 40 is distally reversely curved inwardly, and has a transverse beveled surface 44. Beveled surface 44 and concave inner surface 28 define a latching recess 46, which is adapted for conformally engaging tip section 42 in the course of compressing clip 12 into a latched or locked position around a vessel or other tissue. The top surface of C-shaped hook section 40 (see FIG. 4) comprises two convex surfaces C that come together to define a sharp crest-like cutting edge E to facilitate cutting through connective tissue adjacent a vessel or other tissue during latching of the clip therearound in a manner to be described in greater detail hereinbelow.

Figure 1:
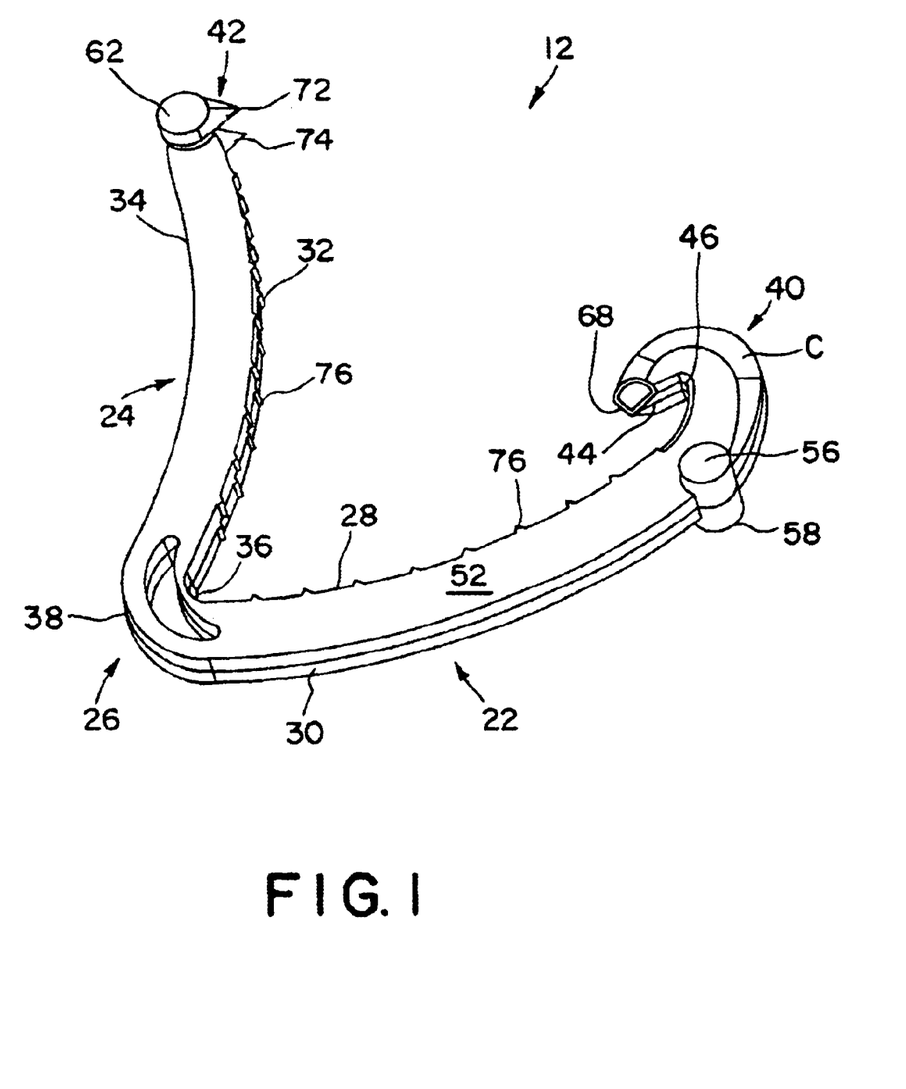
FIG. 1 is an enlarged perspective view of the surgical ligating clip of the present invention.
Figure 2:
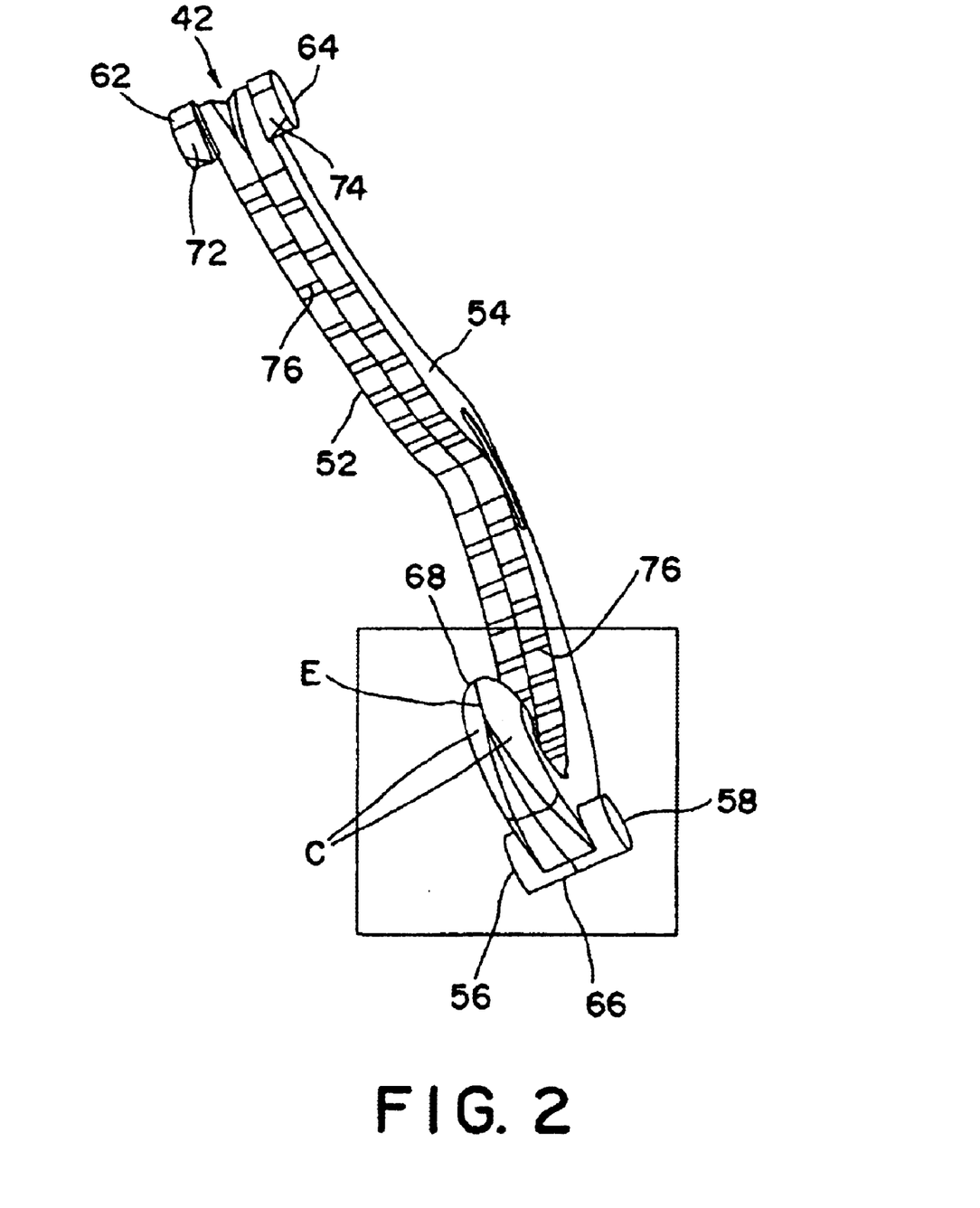
FIG. 2 is another enlarged perspective view of the surgical ligating clip of the present invention.

As best shown in FIG. 2, which is a view directed into the open concave side of clip 12, clip 12 comprises parallel, opposed side surfaces 52 and 54. Typically, the body of clip 12 has a constant thickness between side surfaces 52 and 54. Adjacent to the distal end of the first leg 22 and immediately inwardly of hook section 40, a pair of cylindrical bosses 56 and 58 are formed coaxially on the opposed lateral surfaces of first leg 22. In the illustrated example of clip 12, a bridge section 66 couples bosses 56 and 58 together. As evident in FIG. 2, bosses 56 and 58 project outwardly beyond convex outer surface 30 of first leg 22. Referring still to FIG. 2, at the distal end of second or inner leg 24, another pair of cylindrical bosses 62 and 64 are formed coaxially on the opposed lateral surfaces of inner leg 24 at tip section 42. As evident in FIG. 1, bosses 62 and 64 of second leg 24 extend longitudinally forwardly beyond tip section 42.

Also in the illustrated example of clip 12, hook section 40 of first leg 22 terminates at a sharp tip 68 with cutting edge E extending at least along a portion of the length of the top surface of hook section 40, the distal end of second leg 24 includes a pair of sharp tissue-penetrating teeth 72 and 74, and both first and second legs 22 and 24 have a plurality of protrusions or teeth 76 extending from their respective inner surfaces 28 and 32. These latter features are designed to engage the tissue of the vessel being clamped and assist in preventing the vessel from sliding laterally or longitudinally during or following clip closure. It will be noted, however, that other clips equally suitable for use in conjunction with the invention do not contain such features.

In the practice of ligating a vessel as understood by persons skilled in the art, clip 12 is designed to be compressed into a latched or locked position around the vessel through the use of an appropriate clip applicator instrument, such as the type described in the aforementioned U.S. Pat. No. 5,100,416. The clip applicator instrument engages bosses 56, 58, 62 and 64 of clip 12 and pivots bosses 56, 58, 62 and 64 inwardly about hinge section 26. This causes first and second legs 22 and 24 to close around the vessel, with convex inner surface 32 of second leg 24 and complementary concave inner surface 28 of first leg 22 contacting the outer wall of the vessel. Tip section 42 of second leg 24 then begins to contact hook section 40. Further pivotal movement by the applicator instrument longitudinally elongates first leg 22 and deflects hook section 40, allowing tip section 42 to align with latching recess 46. Upon release of the applicator instrument, tip section 42 snaps into and is conformably seated in latching recess 46, at which point clip 12 is in its latched condition. In the latched condition, tip section 42 is engaged between concave inner surface 28 and beveled surface 44, thereby securely clamping a designated vessel or other tissue between concave inner surface 28 and convex inner surface 32.

Prior art clips similar to clip 12 are described in detail in the commonly assigned U.S. Pat. No. 4,834,096 to Oh et al. and U.S. Pat. No. 5,062,846 to Oh et al., the disclosures of which are incorporated herein in their entireties. In addition, a particularly suitable clip is the HEM-O-LOK® clip commercially available from the assignee of the present invention. These clips are currently available in sizes designated "M", "ML", and "L". The clip cartridge of the invention described hereinbelow can be adapted to accommodate any sizes of HEM-O-LOK® clips commercially available.

Figure 7A:
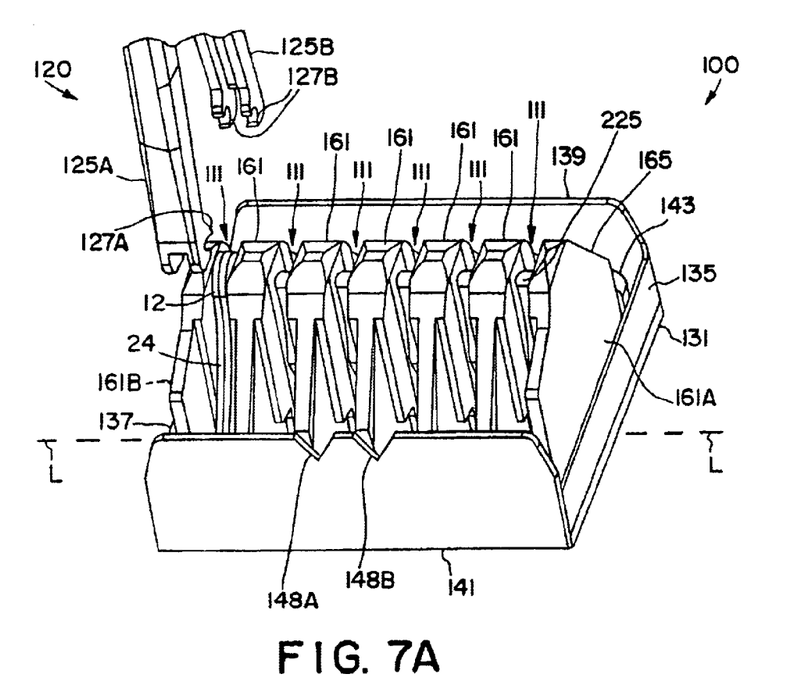
FIG. 7A is a perspective view of a clip applier being inserted into a compartment of a clip cartridge to engage a surgical ligating clip provided in accordance with the present invention.
Figure 7B:
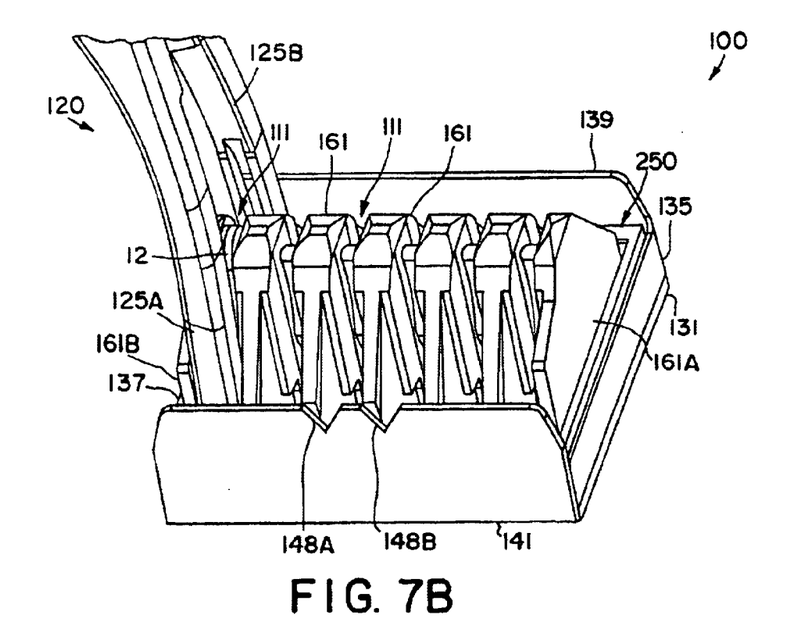
FIG. 7B is another perspective view showing the clip applier engaging the surgical ligating clip loaded in one of the compartments of the clip cartridge as shown in FIG. 7A.
Figure 7C:
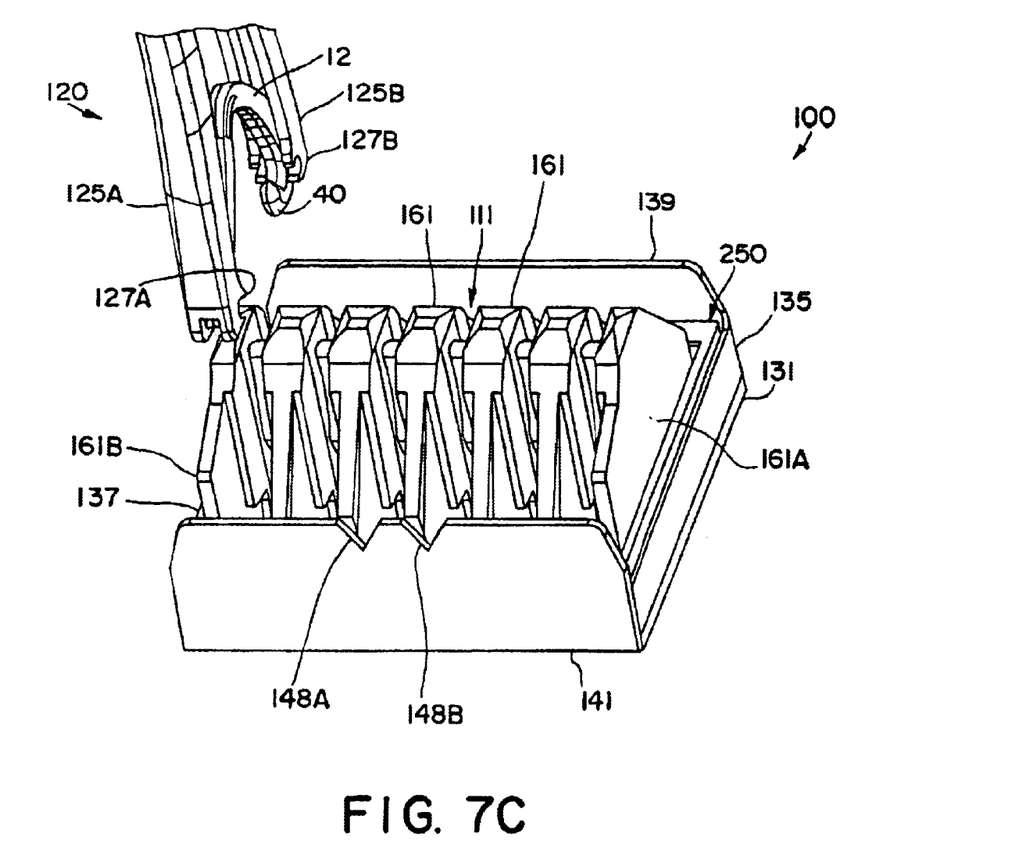
FIG. 7C is another perspective view showing the clip applier extracting the surgical ligating clip from the compartment of the clip cartridge shown in FIG. 7A.

Referring now to FIGS. 7A–7C, a preferred embodiment of a clip cartridge, generally designated 100, is shown for use with clip 12 of the present invention. Clip cartridge 100 preferably is constructed from a single-molded plastic body from which several features are formed. In particular, clip cartridge 100 comprises a plurality of clip retaining chambers or compartments 111 spaced along a longitudinal axis L of clip cartridge 100. Each clip compartment 111 is substantially identical and adapted for storing one clip 12, which preferably has an asymmetric design as described above and illustrated in FIGS. 1–6. FIG. 7A illustrates one clip 12 in a stored condition in one of clip compartments 111. It will be understood, however, that preferred embodiments of clip cartridge 100 include several clip compartments 111 for storing several clips 12. For instance, clip cartridge 100 is adapted for storing six clips 12, although other embodiments can be provided that store more or less clips 12. If desired, an adhesive backing (not shown) can be provided on the underside of clip cartridge 100 to facilitate securing clip cartridge 100 to a tray or other supporting component during use.

FIGS. 7A-7C also illustrate the distal end of a representative clip applying instrument for clip 12, generally designated 120, comprising opposing pivotable jaws 125A and 125B. Jaws 125A and 125B have respective jaw recesses 127A and 127B adapted to engage and retain bosses 56, 58, 62 and 64 of clip 12 (see FIGS. 1–6). According to a method provided by the invention, FIG. 7A illustrates clip applying instrument 120 in a position over clip 12 prior to inserting clip applying instrument 120 into a selected clip compartment 111. FIG. 7B illustrates clip applying instrument 120 being inserted into selected clip compartment 111 to load clip 12 into locking engagement with clip applying instrument 120 (with bosses 56, 58, 62 and 64 retained in jaw recesses 127A and 127B). FIG. 7C illustrates the subsequent step of extracting clip 12 from clip cartridge 100 by removing clip applying instrument 120 with clip 12 loaded therein.

Clip Closure and Tissue Severance

The mechanics of clip closure and connective tissue penetration by the prior art polymeric surgical clip disclosed in the aforementioned U.S. Pat. No. 5,062,846 to Oh et al. will now be described in detail to better understand the present invention. Before any contact is made between the leg members of the prior art polymeric surgical clip, the sharp points of the spaced-apart penetrating members of the second leg start to indent and penetrate the connective tissue therebetween and pull the tissue down, while in between the penetrating members the sharp point of the penetrating member of the hook on the first leg begins to penetrate the tissue and force the tissue up. The sharp point enters the groove on the second leg member and puncturing of the connective tissue begins. The penetrating member of the hook on the end of the first leg is moving through the groove between the penetrating members of the second leg and as penetrating members move closely alongside the sides of the hook portion of the leg, sheer forces contribute to puncturing of the tissue by the tips of the penetrating members of the second leg. After puncture, the knife-like edges of the penetrating members help to tear the connective tissue as the second leg moves down. There is still little or no contact between the penetrating member of the first leg and the groove of the second leg. The tissue caught between the distal end of the second leg and the hook portion begins to stretch. Tissue is jammed between three sharp edges which move in opposite directions. If the tissue is not yet cut between the distal portion of the second leg member and the hook portion, it will be stretched and become thinner and more easily punctured by the sharp point of the distal portion of the hook portion as it passes through the groove and flat beveled surface of the second leg. This point is very sharp and cuts through remaining stretched tissue. In this final stage of cutting and stretching, if all the tissue is not cut, what remains will be quite thin and allow the prior art surgical clip to latch. Although this prior art penetrating surgical clip has been found to effective, the improved penetrating surgical clip 12 of the present invention has been found to be superior in design and function.

Figure 3:
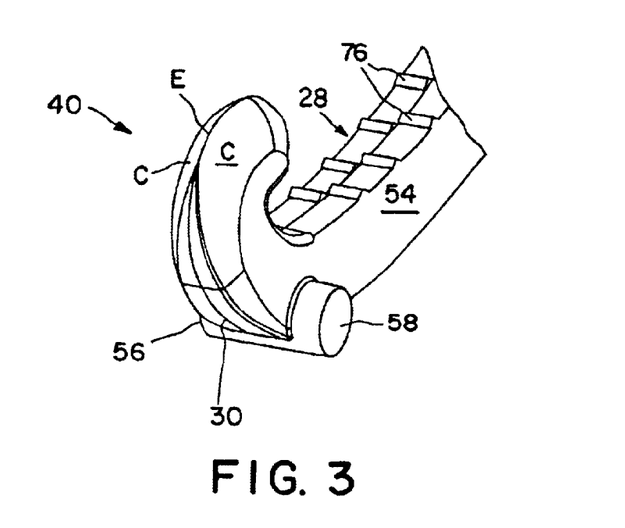
FIG. 3 is an enlarged fragmentary view of the hook member leg of the surgical ligating clip of the present invention.
Figure 4:
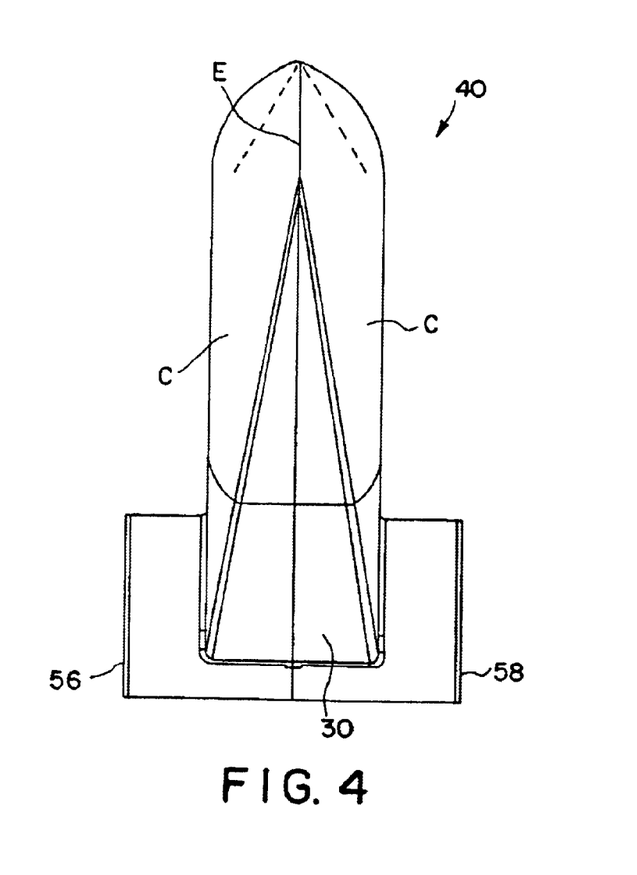
FIG. 4 is a top plan view of the hook member of the surgical ligating clip of the present invention.
Figure 5:
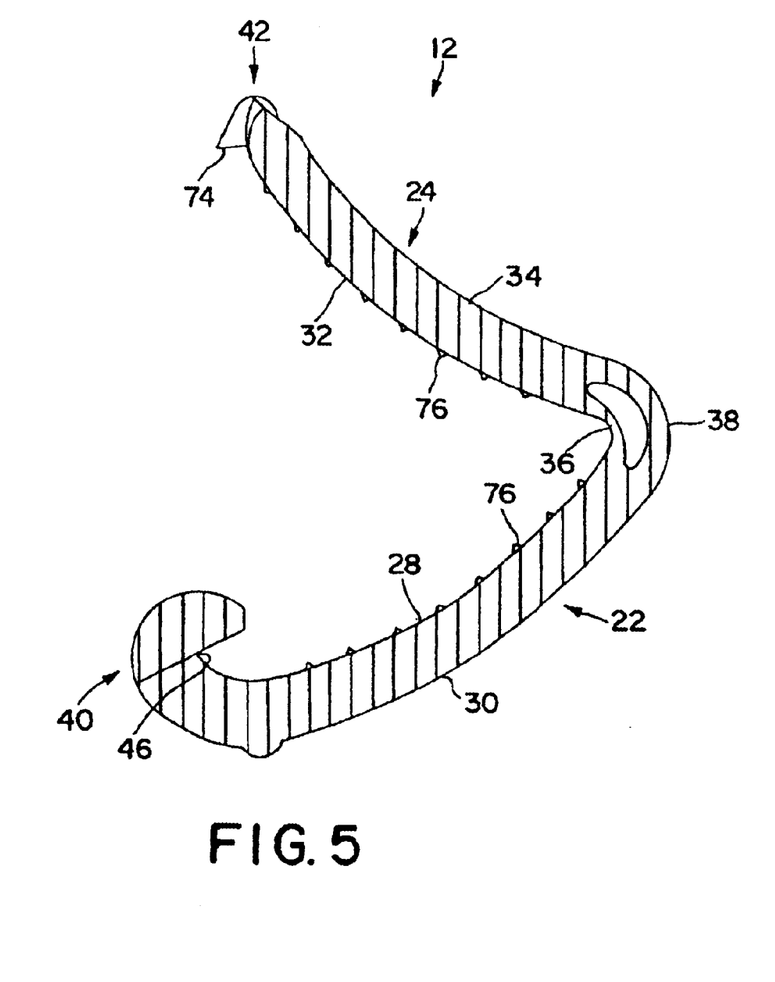
FIG. 5 is a side elevation view of the surgical ligating clip of the present invention.
Figure 6:
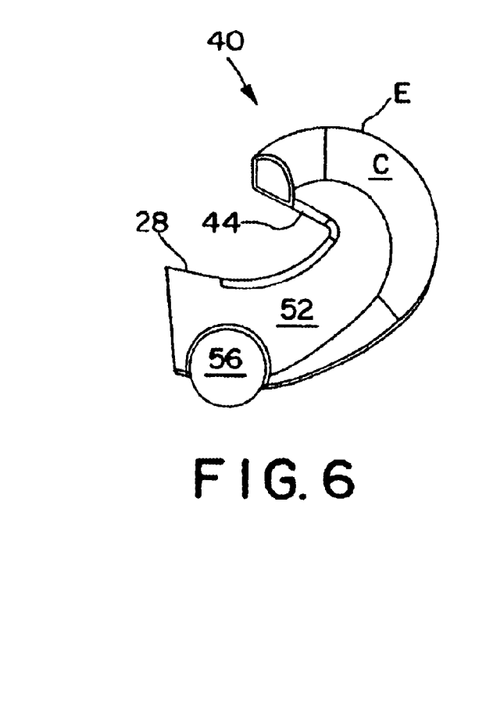
FIG. 6 is a side elevation view of the hook member of the surgical ligating clip of the present invention.

Specifically, the hook element 40 at the end of first leg 22 and the pointed tip section 42 at the end of second leg 24 of clip 12 are adapted for being compressed into a latched or locked position around a vessel or other tissue. Specifically, beveled surface 44 and concave inner surface 28 define a latching recess 46, which is adapted for conformally engaging tip section 42 of the second leg 24 in the course of compressing clip 12 into the latched or locked position around a vessel or other tissue. The stretching, puncturing, and cutting of connective tissue by the distal end of the first leg member and the second leg member as the surgical clip is latched or locked around a vessel or other tissue is somewhat similar to the aforementioned latching action described in the prior art penetrating surgical clip described hereinabove. However, the cutting of connective tissue between the first leg member and the second leg member is significantly superior due to the novel design of hook member 40 at the distal end of first leg member 22. With reference to FIG. 4, two convex surfaces C extend distally from the inner surface of hook member 40 and inwardly from the sides 52, 54 of hook member 40 so as to define a crest or cutting edge E at the juncture thereof along the top portion of the hook member as best shown in FIG. 3 and FIG. 4 of the drawings.

Thus, the large hook end of surgical ligating clip 12 is designed to be able to penetrate through various connective tissues better during closure of the surgical clip. This is accomplished more effectively than prior art clips since leading edge E of the protruding hook member 40 is defined by the termination of two intersecting convex surfaces C. Thus, as surgical clip 12 is closed, leading edge C of hook member 40 contacts the connective tissue and as pressure is applied by closing surgical clip 12, leading edge E slides along the connective tissue and slices into it as first leg member 22 comprising hook member 40 conforms during latching of the surgical clip. The two convex arching surfaces C which create leading edge E of hook member 40 allow for maximum strength and sharpness in the integral hook member cutting edge E.

It will be understood that various details of the invention may be changed without departing from the scope of the invention. Furthermore, the foregoing description is for the purpose of illustration only, and not for the purpose of limitation—the invention being defined by the claims.

What is claimed is:

1. In a polymeric surgical clip comprising first and second leg members joined at their proximal ends by a resilient hinge means, each leg member having a vessel clamping inner surface and an opposite outer surface, said vessel clamping inner surface being in opposition to the vessel clamping inner surface of the other leg member, said first leg member terminating at its distal end in a deflectable hook member curved toward said second leg member, said second leg member terminating at its distal end in a locking portion complementary to said hook member whereby when said first and second leg members are moved from an open position to a closed position about said hinge means, the hook member deflects about the distal end of said second leg member to lock the clip in a closed position, said hook member having a continuously curved outer surface extending distally from said outer surface of said first leg member, side surfaces and an inner surface; the improvement comprising:

the continuously curved outer surface of said hook member comprising two convex surfaces extending distally from the inner surface and inwardly from each side surface of the hook member so that the two convex surfaces define a crest or cutting edge therebetween that extends along the length of at least a portion of the outer surface of the hook member; whereby connective tissue adjacent a vessel or the like to be clamped is cut by the crest or cutting edge of the hook member when said leg members are closed to aid in locking the clip in said closed position.

2. The surgical clip according to claim 1 wherein the inner surface of said first leg member has a concave radius of curvature between the hinge means and the hook member and the outer surface of said first leg member has a convex radius of curvature, the inner surface of the second leg member has a convex radius of curvature between the hinge means and its distal end and the outer surface of said second leg member has a concave radius of curvature between the hinge means and its distal end.

3. The surgical clip according to claim 1 wherein said clip comprises means coupled to said first and second leg members for engagement with a suitable clip applier for applying said clips, said engagement means comprising a pair of bosses joined to opposite sides of said first leg member intermediate said hinge means and said hook portion, and a pair of bosses joined to opposite sides of said second leg member at the distal end of said second leg member, said second leg member having sharp pointed members extending from said bosses.

4. The surgical clip according to claim 3 wherein a portion of said pair of bosses joined to said first leg member extend beyond the outer surface of said first leg member to form substantially parallel and spaced apart surfaces which prevent lateral movement of said first and second leg members relative to one another when the clip is in the closed position.

5. The surgical clip according to claim 4 wherein the inner surfaces of said clip each comprise a plurality of protrusions for providing improved vessel retention during closure of the clips.

6. The surgical clip according to claim 1 wherein said clip further comprises a sharp pointed member attached on each side of the distal end of said second leg member and extending beyond the inner surface of said second leg member, said sharp pointed members of said second leg member cooperating with the cutting edge of said hook member to cut said connective tissue when said clip is moved from said open position to said closed position.

* * * * *

UNITED STATES PATENT AND TRADEMARK OFFICE
CERTIFICATE OF CORRECTION

PATENT NO.       : 6,863,675 B2
APPLICATION NO. :10/251182
DATED            : March 8, 2005
INVENTOR(S)      : Donald F. Wilson, Jr.

It is certified that error appears in the above-identified patent and that said Letters Patent is hereby corrected as shown below:

Delete figs. 7A-7C, and substitute therefor the figs. 7A-7C, as shown on the Attached pages.

Signed and Sealed this

Eighth Day of January, 2008

JON W. DUDAS
*Director of the United States Patent and Trademark Office*